(12) United States Patent
Stott et al.

(10) Patent No.: US 7,439,496 B2
(45) Date of Patent: Oct. 21, 2008

(54) CHEMICAL IDENTIFICATION OF PEROXIDE-BASED EXPLOSIVES

(75) Inventors: William Ronald Stott, Nobleton (CA); Sabatino Nacson, Thornhill (CA); Gabriela Iulia Eustatiu, Streetsville (CA)

(73) Assignee: Smiths Detection Inc., Ontario (CA)

( * ) Notice: Subject to any disclaimer, the term of this patent is extended or adjusted under 35 U.S.C. 154(b) by 338 days.

(21) Appl. No.: 11/417,063

(22) Filed: May 4, 2006

(65) Prior Publication Data

US 2008/0230689 A1 Sep. 25, 2008

Related U.S. Application Data

(60) Provisional application No. 60/678,192, filed on May 6, 2005.

(51) Int. Cl.
*H01J 49/40* (2006.01)

(52) U.S. Cl. ..................... 250/282; 250/288
(58) Field of Classification Search ............... 250/282, 250/288
See application file for complete search history.

(56) References Cited

U.S. PATENT DOCUMENTS

| | | | |
|---|---|---|---|
| 4,378,499 A * | 3/1983 | Spangler et al. | ............. 250/287 |
| 5,037,611 A | 8/1991 | Ledford, Jr. | |
| 5,162,652 A | 11/1992 | Cohen et al. | |
| 5,420,424 A | 5/1995 | Carnahan et al. | |
| 5,741,984 A | 4/1998 | Danylewych-May et al. | |
| 5,859,362 A | 1/1999 | Neudorfl et al. | |
| 5,859,375 A | 1/1999 | Danylewych-May et al. | |
| 5,988,002 A | 11/1999 | Danylewych-May et al. | |
| 6,073,498 A | 6/2000 | Taylor et al. | |
| 6,073,499 A | 6/2000 | Settles | |
| 6,442,997 B1 | 9/2002 | Megerle et al. | |
| 2005/0288616 A1 * | 12/2005 | Bozenbury et al. | ............. 604/1 |

OTHER PUBLICATIONS

Buttigieg, Gavin A. et al., "Characterization of the explosive triacetone triperoxide and detection by ion mobility spetrometry", Forensic Science International, vol. 135, 2003, pp. 53-59.

Evans, Hiram K. et al., "An Unusual Explosive, Triacetonetriperoxide (TATP)", Journal of Forensic Sciences, vol. 31, No. 3, 1986, pp. 1119-1125.

Moore, D. S., "Instrumentation for trace detection of high explosives", Review of Scientific Instruments, vol. 75, No. 8, Aug. 2004, pp. 2499-2512.

* cited by examiner

*Primary Examiner*—Keit T. Nguyen
(74) *Attorney, Agent, or Firm*—Foley & Lardner LLP

(57) ABSTRACT

A method of detecting the presence of an analyte in an ion mobility spectrometer using an amide ionization reagent is provided. This method is particularly useful for the detection of peroxide-based explosives.

12 Claims, 2 Drawing Sheets

CHEMICAL IDENTIFICATION OF PEROXIDE-BASED EXPLOSIVES

BACKGROUND OF THE INVENTION

Trace analyte detection is the detection of small quantities of analytes, often at nanogram to picogram levels. Trace analyte detection can be particularly useful for security applications such as screening individuals or items for components in explosive materials, narcotics and biological warfare agents, where small amounts of these components are deposited on the individual or on the outside of a package or bag. Inherent in the detection of a small quantity of analyte is the possibility of unacceptably high false alarm rates.

Ion mobility spectrometry (IMS) is a well-established technique for the detection of narcotics and explosives. However, due to the sensitivity of the IMS technique, interferences can occur and cause false alarms. If the rate of false alarm is excessive, the practical value of the instrument is diminished due to lack of confidence in the instrument's performance.

False alarms can be caused by detection of trace quantities of an analyte from another source. False alarms can also be caused by chemical signature interferences between substances, such as cosmetics, toiletries, and the like, and an analyte of interest, making it difficult to differentiate an analyte of interest from an interferant.

One way to reduce false alarm rates is by modification of IMS hardware and software. Another means for increasing detection specificity and, thus, reducing false alarm rates is by adjusting the ionization chemistry employed in the IMS by using a different ionization reagent. During the collection of IMS data, a sample is collected, the sample, which may contain an analyte of interest, is introduced into the IMS instrument and then vaporized. The vaporized analytes are directed to an ionization chamber. In the ionization chamber, the analytes are ionized via proton or electron-transfer from ionized reactants. The character of the ionized reactants can affect the type and distribution of analyte ions, altering the IMS signature of an analyte. Reactants can affect the number and size of peaks an analyte produces in an IMS signature and can suppress peaks entirely.

An optimal ionization reagent is capable of forming readily identifiable analyte ions, while suppressing ion formation for molecules which are not of interest. Commonly used IMS reagents include, for example, nicotinamide, ammonia, hexachloroethane, chlorine, 4-Nitrobenzonitrile and water, acetone, and bominated or chlorinated hydrocarbons.

Using common IMS ionization reagents, certain analytes of interest, such as peroxide-based explosives, can be difficult to detect or result in false positive results because this commonly used ionization chemistry does not allow for accurate detection of these explosives.

SUMMARY OF THE INVENTION

Accordingly, there is need in the art for a reagent which results in sample molecule ions that can be accurately detected and characterized and do not result in an excessively high rate of false alarm.

One embodiment provides a method of detecting the presence of an analyte in an ion mobility spectrometer. The method comprises introducing a sample comprising an analyte molecule into an ionization region, supplying an ionization reagent, wherein the ionization reagent has the formula:

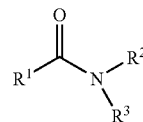

wherein $R^1$ is selected from the group consisting of straight or branched chain alkyl, straight or branched chain alkenyl, aryl, heteroaryl, carbocycle, and heterocycle, wherein $R^2$ and $R^3$ are independently selected from the from the group consisting of H, straight or branched chain alkyl, straight or branched chain alkenyl, aryl, heteroaryl, carbocycle, and heterocycle, and wherein the ionization reagent is not nicotinamide. The method involves generating a reagent ion, allowing the reagent ion to interact with the analyte molecule, wherein the interaction yields an analyte ion, introducing a sample vapor containing at least one analyte ion into a drift region, and detecting the presence of the analyte ion in the sample from a drift time of the analyte ion through the drift region.

These and other features, aspects, and advantages of the present invention will become apparent from the following description, appended claims, and the accompanying exemplary embodiments shown in the drawings, which are briefly described below.

It is to be understood that both the foregoing general description and the following detailed description are exemplary and explanatory only, and are not restrictive of the invention as claimed.

DETAILED DESCRIPTION OF THE PREFERRED EMBODIMENTS

Figure 1:
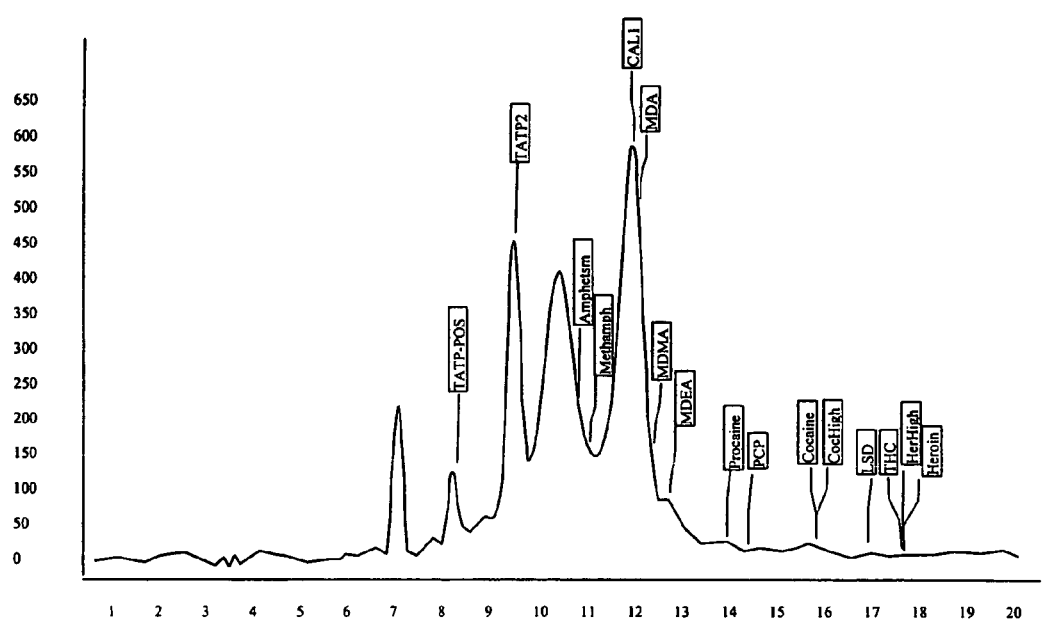
FIG. 1. Plasmagram of TATP obtained using an Ionscan® 500 DT ion mobility spectrometer (Smiths Detection Inc.). Instrument parameters: positive ionization mode, drift tube temperature of 240° C., inlet temperature of 265° C., desorber temperature of 245° C. The ionization reagent is isobutyramide, the drift gas is cleaned, dried room air at a flow rate of 300 cm$^3$/min. The scan period is 24 ms with a 0.200 ms shutter gate pulse, 0.025 s analysis delay, and 8.0 s analysis duration.

A method of detecting trace analytes using novel IMS reagent chemistry with advantageous properties is provided. Specifically, IMS reagents are provided which show suitable sensitivity and selectivity to maximize accurate detection of analytes of interest while suppressing signals from interferants The method involves introducing a sample comprising an analyte molecule into an ionization region, supplying an ionization reagent, generating a reagent ion, allowing the reagent ion to interact with the analyte molecule to produce an analyte ion, introducing a sample vapor containing at least one analyte ion into a drift region, and detecting the presence of the analyte ion in the sample from a drift time of the analyte ion through the drift region.

Unless indicated otherwise, all technical and scientific terms are used in a manner that conforms to common technical usage. Generally, the nomenclature of this description and the described procedures and techniques are well known and commonly employed in the art. "Approximately," as it is used herein, generally refers to a variation of 10% to 20% from a given value and is meant to allow for error inherent in measurement techniques as well as differences in measurement values that can be obtained when measurements are performed using different techniques.

"Sample" refers, without limitation, to any molecule, compound or complex that can be introduced into an IMS instrument. A sample can contain an analyte of interest, referred to herein as an "analyte" or "sample analyte," which is understood to be any analyte to be detected using a detection technique.

Analysis of analytes in a sample begins with collection of a sample and introduction of the sample into the spectrometer. A sample can be introduced into an IMS instrument using any suitable method. A variety of different methods can be used to introduce a sample into a detection instrument and the method will depend, in part, on the type of sample being analyzed. For example, U.S. Pat. Nos. 6,442,997, 6,073,499, 5,859,362, and 5,162,652 disclose devices for collecting vapor or air samples, U.S. Pat. No. 6,073,498 discloses a device for collecting fluid samples, U.S. Pat. No. 5,037,611 is directed to a method adsorbing gaseous samples on a tape, and U.S. Pat. No. 5,741,984 discloses a method which introduces a sample from a finger by pressing the finger on a sampling "token." U.S. Pat. Nos. 5,859,375 and 5,988,002 are directed to a methods and apparatus for collecting samples using a hand-held sampling device.

Another sampling method involves contacting an object or other substrate to be tested with a fabric sampling swab which collects analyte particles. Upon contact of a sampling swab with a substrate to be tested, solid sample particles can become imbedded into the porous structure of the textile swab. If the sample is in liquid form, the liquid can absorb into the fibers of the swab. In IMS, the swab is placed into the detection instrument and the sample thermally desorbed from the swab.

A sample can be desorbed transforming analyte from solid, liquid or preconcentrated into a gaseous state suitable for ionization and subsequent analysis in an IMS instrument. Desorption can be accomplished using any suitable desorber, such as, for example, a heater which vaporizes the sample. The sample is then swept by a gas flow into an ionization region or ionization chamber.

Within the ionization chamber, a sample analyte is ionized. Analyte ionization can be accomplished by ionizing a reagent which serves to ionize an analyte. This primary ionization can be accomplished using any suitable ionization source. Suitable sources include radioactive sources, such as $^{63}$Ni, $^{241}$Am and $^{3}$H. Others ionizers, including, but not limited to corona discharge ionization and electrospray ionization, can also be used. Ionized reactants can then interact in the gas phase with analytes transferring protons or electrons to analyte molecules and forming analyte ions.

Amides useful as ionization reagents for trace detection include amides having the following formula:

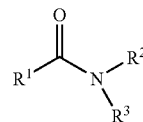

wherein $R^1$ can be straight or branched chain alkyl, straight or branched chain alkenyl, aryl, heteroaryl, carbocycle, or heterocycle. $R^2$ and $R^3$ are independently selected from the from the group consisting of H, straight or branched chain alkyl, straight or branched chain alkenyl, aryl, heteroaryl, carbocycle, and heterocycle. In one embodiment, $R^1$ is a phenyl or aniline group, and $R^2$ and $R^3$ is independently selected from the from the group consisting of straight or branched chain alkyl, straight or branched chain alkenyl, aryl, heteroaryl, carbocycle, and heterocycle. In a further embodiment, $R^2$ is $CH_3$ and $R^3$ is $C_2H_5$. In another embodiment, $R^2$ is phenyl and $R^3$ is an alkyl having the general formula $C_nH_{(2n+1)}$. In yet another embodiment, the amide is 2-methylpropionamide (common name: isobutyramide). The contemplated amide ionization reagent does not include nicotinamide.

Amides are useful ionization reagents in the detection of a wide range of analytes, including but not limited to explosives, narcotics, chemical warfare agents, toxins, and other chemical compounds. "Analyte" or "sample analyte" is understood to be any analyte to be detected using a detection technique.

Amide ionization chemistry is useful for the detection of peroxide-based explosives. Peroxide-based explosives for which amide ionization chemistry is useful include hexamethylenetriperoxidediamine (HMTD) and triacetone triperoxide (TATP).

Narcotics for which amide ionization chemistry is useful include, but are not limited to, 6-acetylmorphine, alprazolam, amobarbital, amphetamine, antipyrine, benzocaine, benzoylecgonine, bromazepam, butalbital, carbetapentane, cathinone, chloradiazepoxide, chlorpheniramine, cocaethylene, cocaine, codeine, diazepam, ecgonine, ecognine methyl ester (EME), ephedrine, fentanyl, flunitrazepam, hashish, heroin, hydrocodone, hydromorphone, ketamine, lidocaine, lorazepam, lysergic acid diethylamide (LSD), lysergic acid, N-methyl-1-3(3,4-methylenedioxyohenyl)-2-butanamine (MBDB), 3,4-methylenedioxyamphetamine (MDA), DL-3,4-methylenedioxyethylamphetamine (MDEA), methylenedioxymethamphetamine (MDMA), marijuana, mescaline, methadone, methamphetamine, methaqualone, methcathinone, morphine, noscapine, opium, oxazepam, oxycodone, phencyclidine (PCP), pentobarbital, phenobarbital, procaine, psilocybin, secobarbital, temazepam, THC, THC—COOH, triazolam, pharmaceutical drugs, and combinations thereof.

Chemical warfare agents for which an amide ionization reagent is useful include, but are not limited to amiton (VG), anthrax, chloropicrin, ethyl N,N-dimethyl phosphoramicocyanidate (Tabun), isopropyl methyl phosphonofluoridate (Sarin), pinacolyl methyl phosphonefluoridate (Soman), ethyl-, isopropyl ester (GE), ethyl-, S-(2-(diethylamino) ethyl) O-ethyl ester (VE), phosphonothioic acid, methyl-, S-(2-(diethylamino)ethyl) O-ethyl ester (VM), mustard-T mixture, nitrogen mustard 1, nitrogen mustard 2, nitrogen mustard 3, phenyldichloroarsine, phosgene oxime, sesqui mustard, adamsite, aflatoxin, botulinus toxin, ricin, saxitoxin, trichothecene mycotoxin, methylphosphonothioic acid S-(2-

(bis(1-methylethyl)amino)ethyl) O-ethyl ester (VX), cyclohexyl methylphosphonofluoridate (GF), and combinations thereof.

The identification of analyte ions is accomplished using any suitable means, such as, for example a standard IMS instrument. The fundamental design and operation of an ion mobility spetectometer is addressed in, for example, Ion Mobility Spectrometry (G. Eiceman and Z. Karpas, CRC Press, Boca Raton, Fla., 1994). Ions are spatially separated in the IMS drift region in accordance to their ion mobility, which is an intrinsic property of an ion. Detection can occur, for example, by monitoring an induced current at the collector which generates a signature for each ion as a function of the time required for that ion to reach the collector. This signature is used to identify a specific analyte.

The following example is illustrative. It should be understood, however, that the invention, as claimed, is not limited to the specific embodiments described in this example. It will be apparent to those skilled in the art that various modifications and variations can be made to the embodiments of the claimed invention without departing from the spirit or scope of the claimed invention. Thus, it is intended that the claimed invention covers other modifications and variations of this invention within the scope of the appended claims and their equivalents.

EXAMPLE 1

Figure 2:
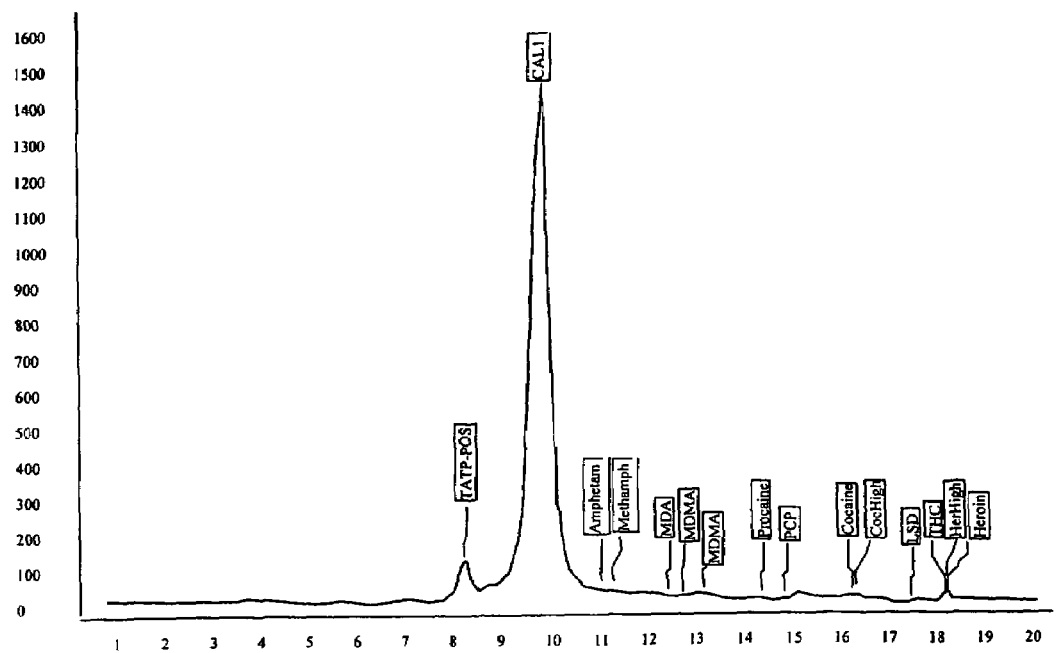
FIG. 2. Plasmagram of TATP obtained using an Ionscan® 500 DT ion mobility spectrometer (Smiths Detection Inc.). Instrument parameters: positive ionization mode, drift tube temperature of 250° C., inlet temperature of 265° C., desorber temperature of 245° C. The ionization reagent is nicotinamide, the drift gas is cleaned, dried room air at a flow rate of 350 cm$^3$/min. The scan period is 24 ms with a 0.200 ms shutter gate pulse, 0.025 s analysis delay, and 8.00 s analysis duration.

IMS Signature of TATP Using Nicotinamide and Isobutyramide Ionization Reagents This example demonstrates the difference in the TATP IMS signature when isobutyramide is used as an ionization reagent as compared to nicotinamide. FIGS. 1 and 2 each show the IMS spectrum of TATP using isobutyramide and nicotinamide, respectively. The TATP samples used with each of the ionization reagents are prepared identically. The plasmagrams are obtained using Ionscan® 500 DT ion mobility spectrometer (Smiths Detection Inc.) run with following parameters: positive ionization mode, drift tube temperature of 230° C., inlet temperature of 265° C., desorber temperature of 245° C. The ionization reagent is isobutyramide, the drift gas is cleaned, dried room air at a flow rate of 300 cm$^3$/min. The scan period is 24 ms with a 0.200 ms shutter gate pulse, 0.025 s analysis delay, and 8.00 s analysis duration. The two stage analysis uses 5 co-added scans per segment and 8 segments per analysis and 20 co-added scans per segment and 12 segments per analysis.

A comparison of a plasmagram obtained with isobutyramide as compared with nicotinamide shows that at least two peaks are obtained when isobutyramide is used as the ionization reagent, whereas only one peak is obtained when nicotinamide is used as the ionization reagent. When sampling TATP, the presence of two peaks allows for more selective determination of TATP and minimizes the rate of false alarms.

What is claimed is:

1. A method of detecting the presence of an analyte in an ion mobility spectrometer comprising:
   (a) introducing a sample comprising one or more analyte molecules into an ionization region
   (b) supplying an ionization reagent, wherein the ionization reagent has the formula:

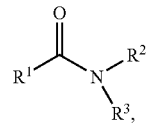

wherein $R^1$ is selected from the group consisting of straight or branched chain alkyl, straight or branched chain alkenyl, aryl, heteroaryl, carbocycle, and heterocycle,
   wherein $R^2$ and $R^3$ are independently selected from the group consisting of H, straight or branched chain alkyl, straight or branched chain alkenyl, aryl, heteroaryl, carbocycle, and heterocycle, and
   wherein the ionization reagent is not nicotinamide;
   (c) generating a reagent ion;
   (d) allowing the reagent ion to interact with the one or more analyte molecules, wherein the interaction yields one or more analyte ions;
   (e) introducing a sample vapor containing one or more analyte ions into a drift region; and
   (f) detecting the presence of the one or more analyte ions in the sample from a drift time of the analyte ion through the drift region.

2. The method of claim 1, wherein $R^1$ is a $C_3$ alkyl, and wherein $R^2$ and $R^3$ are H.

3. The method of claim 2, wherein the amide is isobutyramide.

4. The method of claim 1, wherein $R^1$ is a phenyl or an aniline group, and wherein $R^2$ and $R^3$ are independently selected from the group consisting of straight or branched chain alkyl, straight or branched chain alkenyl, aryl, heteroaryl, carbocycle, and heterocycle.

5. The method of claim 1, wherein $R^2$ is $CH_3$, and wherein $R^3$ is $C_2H_5$.

6. The method of claim 1, wherein $R^2$ is a phenyl and $R^3$ is a $C_nH_{(2n+1)}$ alkyl.

7. The method of claim 1, wherein more than one analyte ion for a single analyte is produced, wherein each of more than one analyte ions demonstrate a different drift time.

8. The method of claim 1, wherein the analyte is selected from the group consisting of explosive, narcotic, biological warfare agent, toxin, and chemical warfare agent.

9. The method of claim 8, wherein the explosive is selected from the group consisting of hexamethylenetriperoxidediamine, triacetone triperoxide, and combinations thereof.

10. The method of claim 9, wherein the explosive is triacetone triperoxide.

11. The method of claim 8, wherein the narcotic is selected from the group consisting of 6-acetylmorphine, alprazolam, amobarbital, amphetamine, antipyrine, benzocaine, benzoylecgonine, bromazepam, butalbital, carbetapentane, cathinone, chloradiazepoxide, chlorpheniramine, cocaethylene, cocaine, codeine, diazepam, ecgonine, ecognine methyl ester (EME), ephedrine, fentanyl, flunitrazepam, hashish, heroin, hydrocodone, hydromorphone, ketamine, lidocaine, lorazepam, lysergic acid diethylamide (LSD), lysergic acid, N-methyl-1-3(3,4-methylenedioxyohenyl)-2-butanamine (MBDB), 3,4-methylenedioxyamphetamine (MDA), DL-3, 4-methylenedioxyethylamphetamine (MDEA), methylenedioxymethamphetamine (MDMA), marijuana, mescaline, methadone, methamphetamine, methaqualone, methcathinone, morphine, noscapine, opium, oxazepam, oxycodone, phencyclidine (PCP), pentobarbital, phenobarbital, procaine, psilocybin, secobarbital, temazepam, THC, THC—COOH, triazolam, pharmaceutical drugs, and combinations thereof.

12. The method of claim 8, wherein the chemical warfare agent or toxin is selected from the group consisting of amiton (VG), anthrax, chloropicrin, ethyl N,N-dimethyl phosphoramicocyanidate (Tabun), isopropyl methyl phosphonofluoridate (Sarin), pinacolyl methyl phosphonefluoridate (Soman), ethyl-, isopropyl ester (GE), ethyl-, S-(2-(diethylamino)ethyl) O-ethyl ester (VE), phosphonothioic acid, methyl-, S-(2-(diethylamino)ethyl) O-ethyl ester (VM), mustard-T mixture, nitrogen mustard 1, nitrogen mustard 2, nitrogen mustard 3, phenyldichloroarsine, phosgene oxime, sesqui mustard, adamsite, aflatoxin, botulinus toxin, ricin, saxitoxin, trichothecene mycotoxin, methylphosphonothioic acid S-(2-(bis(1-methylethyl)amino)ethyl) O-ethyl ester (VX), cyclohexyl methylphosphonofluoridate (GF), and combinations thereof.

* * * * *